(12) United States Patent
Lorant

(10) Patent No.: US 6,383,998 B1
(45) Date of Patent: May 7, 2002

(54) COMPOSITION COMPRISING A VOLATILE FLUORO COMPOUND AND A PROCESS FOR REMOVING MAKE-UP FROM THE SKIN OR CLEANSING THE SKIN

(75) Inventor: Raluca Lorant, Thiais (FR)

(73) Assignee: L'Oréal, Paris (FR)

( * ) Notice: Subject to any disclaimer, the term of this patent is extended or adjusted under 35 U.S.C. 154(b) by 138 days.

(21) Appl. No.: 09/609,933

(22) Filed: Jun. 30, 2000

(30) Foreign Application Priority Data

Jun. 30, 1999 (FR) .............................. 99 08373

(51) Int. Cl.$^7$ .............................. C11D 3/24; B08B 3/04
(52) U.S. Cl. .................. 510/136; 134/40; 510/130; 424/59; 424/61; 424/64; 424/401
(58) Field of Search ................. 510/130, 136; 424/401, 59, 61, 64; 134/40

(56) References Cited

U.S. PATENT DOCUMENTS

| | | |
|---|---|---|
| 5,523,091 A | 6/1996 | Pastour et al. |
| 5,993,832 A | 11/1999 | Lorant et al. |
| 6,224,851 B1 * | 5/2001 | Bara |
| 6,251,375 B1 * | 6/2001 | Bara |

FOREIGN PATENT DOCUMENTS

| | | |
|---|---|---|
| EP | 0 503 853 | 9/1992 |
| EP | 0 827 736 | 3/1998 |
| EP | 0 930 059 | 7/1999 |
| FR | 2 280 360 | 2/1976 |
| FR | 2 701 845 | 9/1994 |
| FR | 2 705 894 | 12/1994 |
| FR | 2 745 715 | 9/1997 |

OTHER PUBLICATIONS

Patent Abstracts of Japan, vol. 13, No. 211, May 17, 1989, JP 01 031708.
Derwent Publications Ltd., London, GB; AN 1988–103046, XP002135440, Mar. 8, 1988.
English language Derwent Abstract of EP 0 827 736. Jul. 28, 1997.
English language Derwent Abstract of EP 0 930 059. Dec. 22, 1998.
English language Derwent Abstract of FR 2 280 360. Apr. 2, 1976.
English language Derwent Abstract of FR 2 745 715. Sep. 15, 1978.

* cited by examiner

Primary Examiner—Yogendra N. Gupta
Assistant Examiner—Gregory E. Webb
(74) Attorney, Agent, or Firm—Finnegan, Henderson, Farabow, Garrett & Dunner, L.L.P.

(57) ABSTRACT

An anhydrous or aqueous composition containing at least one volatile fluoro compound in an amount of at least 0.5% by weight, and a process for make-up removal or for cleansing the skin, comprising (1) applying, preferably with the fingers, a pad of cotton wool, or a paper tissue, a sufficient amount of the composition to the parts of the skin to be cleansed or from which make-up is to be removed, (2) lightly massaging so as to detach the maximum amount of impurities and of the make-up product, and (3) removing the composition using a pad of cotton wool optionally soaked in water.

31 Claims, No Drawings

COMPOSITION COMPRISING A VOLATILE FLUORO COMPOUND AND A PROCESS FOR REMOVING MAKE-UP FROM THE SKIN OR CLEANSING THE SKIN

The present invention relates to a process for removing make-up from the skin or for cleansing the skin, in particular the face, using an anhydrous or aqueous cosmetic composition which comprises at least one volatile fluoro compound. More particularly, the present invention relates to the use of a composition in the form of a make-up-removing milk, cream, or oil. The invention also relates to a cosmetic composition in the form of a water-in-oil (W/O) or oil-in-water (O/W) emulsion.

The removal of make-up essentially involves dissolving and removing all the traces of make-up as well as the impurities accumulated on the face originating from atmospheric pollution. It is important, during make-up removal, to cleanse the skin well without attacking it.

The removal of make-up is usually carried out with the aid of fluid products based on surfactants, generally in aqueous solution or in the form of an emulsion. Although these make-up-removing products allow good removal of standard "non-waterproof" make-up, they nevertheless can have the drawback of drying out the skin by removing its natural hydrolipid film, and of causing certain skin irritations, particularly on the most sensitive parts of the face such as the eyelids, around the eyes, and the lips. Make-up-removing products based on detergent surfactants can thus be disadvantageous for the removal of make-up from sensitive and delicate skin.

On the other hand, make-up of the "waterproof" type requires the use of specific make-up-removing agents which comprise an oil, such as, for example, liquid petroleum jelly in combination with fatty esters. However, these make-up-removing products have disadvantages on application, such as a greasy sensation on the skin, which are such that, when they are not essential, it is preferred to use standard make-up-removing products even though these standard products may lack efficacy.

After extensive studies on various types of compounds, it has now been found, surprisingly and unexpectedly, that the use of certain volatile fluoro compounds in such compositions makes it possible to afford particularly high-quality make-up-removing properties, while at the same time imparting the effect of freshness after application. Furthermore, it has been found that when these make-up-removing compositions are in the form of an emulsion, they can be advantageously formulated in the presence of a small proportion of a detergent surfactant without thereby impairing their make-up-removing power, consequently making it possible to obtain better cosmetic properties in terms of pleasantness and comfort. Another particularly appreciable advantage of these novel compositions lies in the fact that they can be capable of removing the various types of make-up, e.g. waterproof, non-waterproof, and "transfer-resistant" make-up, and of doing so under highly satisfactory conditions.

A subject of the present invention is thus a process for removing make-up from or for cleansing the skin, using an anhydrous or aqueous composition, wherein the composition comprises at least one volatile fluoro compound in an amount of at least 0.5% by weight, relative to the total weight of said composition.

According to the invention, the volatile fluoro compound is preferably present in the composition in an amount of at least 5%, more preferably from 5 to 80%, and even more preferably from 8 to 70% by weight relative to the total weight of the composition.

The volatile fluoro compounds which can be used according to the invention and which may be of oily type are preferably chosen from the following:

1) Perfluorocycloalkyls corresponding to formula (I):

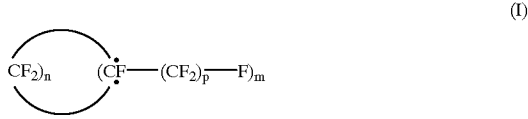

(I)

in which:
   n is 3, 4 or 5,
   m is 1 or 2, and
   p is 1, 2 or 3,
   with the proviso that when m=2, the groups (CF—(CF$_2$)$_p$—F) are not necessarily alpha to each other;

2) Perfluoroalkanes corresponding to formula (II):

(II)

in which:
   m is 2 to 8, and
   X is chosen from Br or F;

3) Fluoroalkyls and heterofluoroalkyls corresponding to formula (III):

(III)

in which:
   t is 0 or 1,
   n is 0, 1, 2 or 3,
   X is chosen from linear and branched perfluoroalkyl radicals containing from 2 to 5 carbon atoms, and
   Z is chosen from O, S, or NR, wherein R is chosen from hydrogen and the radicals —(CH$_2$)$_n$—CF$_3$ and —(CF$_2$)$_m$—CF$_3$, wherein m is 2, 3, 4, or 5, and 4) Perfluoromorpholine derivatives corresponding to formula (IV):

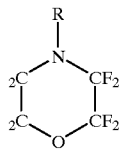

(IV)

in which:
   R is a C$_1$–C$_4$ perfluoroalkyl radical.

Among the perfluorocycloalkyls of formula (I) useful according to the invention are, for example, perfluoromethylcyclopentane and perfluoro-1,3-dimethylcyclohexane, which are sold under the names "Flutec PC1®" and "Flutec PC3®" by the company BNFL Fluorochemicals Ltd., and perfluoro-1,2-dimethylcyclobutane.

Among the perfluoroalkanes of formula (II) useful according to the invention are, for example, dodecafluoropentane and tetradecafluorohexane, which are sold under the names "PF5050®" and "PF5060®" by the company 3M, or alternatively, bromoperfluorooctyl sold under the name "Foralkyl®" by the company Atochem.

Among the fluoro compounds of formula (III) useful according to the invention are, for example, nonafluoromethoxybutane sold under the name MSX 4518®" by the company 3M, and nonafluoroethoxyisobutane.

Finally, among the perfluoromorpholine derivatives of formula (IV) useful according to the invention is, for example, is 4-trifluoromethylperfluoromorpholine, sold under the name "PF5052®" by the company 3M.

The fluoro compounds described above are further characterized by their high density, which is generally greater than 1, and preferably greater than 1.2, by a saturating vapour pressure at 25° C., at least equal to 50 Pa, and by a boiling point generally from 25 to 65° C.

When, according to the invention, an anhydrous composition is used, it is essentially an oil, and the volatile fluoro compound is present either in soluble form or in a form which is finely dispersed in at least one cosmetic oil.

Among the non-fluoro oils which are miscible with the volatile fluoro compound, are, for example, polysiloxanes, in particular PDMSs, especially volatile ones such as cyclopentasiloxane and cyclohexasiloxane, volatile hydrocarbon-based oils, particularly $C_{11}$–$C_{13}$ isoparaffins, and isododecane.

Among the non-fluoro oils which are immiscible with the volatile fluoro compound, are, for example, fatty acid esters containing at least 6 carbon atoms, which are preferably obtained from a linear and branched $C_1$–$C_{17}$ alcohol and from a linear and branched $C_6$–$C_{22}$ fatty acid, preferably a fatty mono- or diacid. Among these esters, mention may be made of 2-ethylhexyl palmitate, 2-ethylhexyl myristate, isopropyl palmitate, isopropyl myristate, diisopropyl adipate, dioctyl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate, isopropyl isostearate, and mixtures thereof.

According to this embodiment, the concentration of volatile fluoro compound is generally from 20 to 80%, and preferably from 30 to 65%, relative to the total weight of the composition when it is in the form of oil.

When an aqueous cosmetic composition is used according to the invention, it is in the form of multiple emulsions, but preferably in the form of a W/O or O/W emulsion containing a fatty phase, an aqueous phase, and optionally a surfactant, wherein the fatty phase contains the volatile fluoro compound.

The emulsions constitute a preferred embodiment for removing make-up from the skin and for cleansing the skin. The emulsions preferably contain, relative to the total weight of the emulsion, from 2 to 70%, but preferably from 5 to 30%, fatty phase by weight, and from 30 to 98%, but preferably from 70 to 95%, aqueous phase by weight. The amount of volatile fluoro compound in the fatty phase generally ranges from 10 to 100%, but preferably from 30 to 95%, and even more preferably from 40 to 80%, by weight relative to the total weight of the said phase.

The fatty phase of the emulsions according to the invention may be in the form of a mixture of volatile fluoro compound with at least one non-fluoro cosmetic oil, which is miscible or immiscible with the volatile fluoro compound, in an amount ranging from 0.5 to 60%, preferably from 1 to 40%, by weight relative to the total weight of the said phase. The non-fluoro oils, which are miscible or immiscible with the volatile fluoro compound of the fatty phase of the emulsions, can be chosen, for example, from those mentioned previously.

The aqueous phase of the emulsions can also contain any water-soluble ingredient commonly used in cosmetic emulsions. Mention may be made, for example, of moisturizers such as glycerol and propylene glycol.

As indicated previously, the emulsions according to the present invention have excellent intrinsic make-up-removing power in the absence of detergent surfactant. However, they can contain a small proportion of detergent surfactant, which can be present for the purpose of ensuring satisfactory stability of the emulsion. According to this embodiment, the surfactant is generally present in an amount ranging from 0.2 to 8% by weight of active material, relative to the total weight of the emulsion.

When the make-up-removing compositions are in the form of an O/W emulsion, the surfactant is preferably an anionic or amphoteric surfactant comprising at least one phosphate, sulfate, or acetylmethyltaurate group, such as those described in patent application FR-2 745 715. Among these surfactants are, for example, those sold under the names "Pecosil PS-100®," Pecosil PS-200®," and "Pecosil WDS-100®" by the company Phoenix Chemical.

When the make-up-removing emulsions are of the W/O type, they then preferably contain silicone surfactants, in particular those belonging to the alkyl- or alkoxydimethicone copolyol family, or alternatively, dimethicone copolyols such as those described in patent application FR-2 701 845. Among these surfactants are, for example, those sold under the names "Abil WE09®," "Abil WS08®," and "Abil EM90®" by the company Goldschmidt, "Q2 5200®" or "Q2 3225®" by the company Dow Corning, and "218-1138®" or "SF 1228®" by the company General Electric.

The emulsions according to the invention are more or less fluid, and more particularly have the appearance of a milk or a cream. The preparation of the make-up-removing or cleansing milks or creams is generally made easier by the use of a thickener, which is then present in an amount ranging from 0.1 to 5% by weight, relative to the total weight of the composition in milk or cream form.

The thickener can be chosen, for example, from:

(a) polysaccharide biopolymers such as xanthan gum, carob gum, guar gum, alginates, and modified celluloses such as hydroxyethylcellulose, methylcellulose, hydroxypropylcellulose, and carboxymethylcellulose, and (b) synthetic polymers, for example polyacrylic acids such as the polyglyceryl (meth)acrylate polymers sold under the names "Hispagel®," "Lubragel®," or "Sepigel 305®," respectively, by the companies Hispano Quimica, Guardian, and SEPPIC, polyvinylpyrrolidone, polyvinyl alcohol, crosslinked polymers of acrylamide and ammonium acrylate sold under the names "PAS 5161 e" or "Bozepololl®" by the company Hoechst, crosslinked polymers of acrylamide and methacryloyloxyethyl-trimethylammonium chloride sold under the name "Salcare SC 92®" by the company Allied Colloids, and magnesium aluminium silicate.

The thickeners preferably used are the crosslinked polymers of acrylamide and 2-acrylamido-2-methylpropanesulphonic acid, also known as AMPS, which are partially or totally neutralized, and which are sold under the name "Hostacerin AMPS®" by the company Clariant. These thickeners are described, for example, in patent application EP-503 853, the content of which is incorporated herein by reference.

The compositions according to the invention as defined above can also comprise any conventional cosmetic ingredient such as, for example, preserving agents, antioxidants, fragrances, soluble dyes, or active principles which have, for example, emollient, regenerating, decongesting, anti-inflammatory, lightening, detoxifying, cicatrizing, or softening activity.

The present invention moreover relates to a process for removing make-up from the skin or for cleansing the skin, which comprises (1) applying, preferably with the fingers, a pad of cotton wool, or a paper tissue, a sufficient amount of the composition as defined above, to the parts of the skin to be cleansed or from which make-up is to be removed, (2) lightly massaging so as to detach the maximum amount of impurities and of the make-up product, and (3) removing the composition using a pad of cotton wool optionally soaked in water.

Several non-limiting examples of make-up-removing or cleansing compositions for the face, according to the invention, will now be given.

EXAMPLES

Example 1
Make-up-removing Oily Lotion

An oily anhydrous make-up-removing lotion was prepared by mixing together the following ingredients:

| | |
|---|---|
| Nonafluoromethoxybutane | 40.0% |
| Tetradecafluorohexane | 20.0% |
| Cyclohexasiloxane | 40.0% |

This lotion, which was homogeneous and clear, allowed, when applied using a pad of cotton wool to the parts of the face from which make-up was to be removed, excellent removal of the make-up while at the same time providing freshness and softness.

Example 2
Make-up-removing Milk

A make-up-removing milk was prepared by mixing together the following ingredients:

| | |
|---|---|
| A-Fatty phase | |
| Nonafluoromethoxybutane | 10.0% |
| B-Aqueous phase | |
| Xanthan gum | 0.2% |
| Sodium dimethicone copolyol acetyl methyl laurate sold under the trade name "Pecosil DCT ® " by the company Phoenix Chemical | 5.4% |
| Preserving agents | 0.2% |
| Water | 84.8% |

This make-up-removing milk was applied to the entire face, coated all traces of the make-up and impurities, and left the skin cleansed deep-down, supple and very fresh.

Example 3
Make-up-removing Cream

Make-up-removing cream was prepared by mixing together the following ingredients:

| | |
|---|---|
| A-Fatty phase | |
| Tetradecafluorohexane | 10.0% |
| Cycohexasiloxane | 5.0% |
| B-Aqueous phase | |
| AMPS polymer sold under the name "Hostacerin AMPS ® " by the company Clariant | 2.0% |
| Preserving agents | 0.2% |
| Water | 82.8% |

This cream, which was free of surfactant, was particularly suitable for sensitive skin since it dissolved impurities and waterproof and non-waterproof make-up gently, while at the same time respecting the integrity of the skin hydrolipid film.

Example 4
Make-up-removing Emulsion

A make-up-removing emulsion was prepared by mixing together the following ingredients:

| | |
|---|---|
| A-Fatty phase | |
| Nonafluoromethoxybutane | 20.0% |
| B-Aqueous phase | |
| Sodium dimethicone copolyol acetyl methyl laurate sold under the trade name "Pecosil DCT ® " by the company Phoenix Chemical | 5.4% |
| Preserving agents | 0.2% |
| Xanthan gum | 0.2% |
| Water | 74.2% |

When this emulsion was applied using a pad of cotton wool to the parts of the face to be cleansed, excellent removal of the make-up was obtained, the skin remained supple with a sensation of freshness.

Example 5
Make-up-removing Cream

A make-up-removing cream was prepared by mixing together the following ingredients:

| | |
|---|---|
| A-Fatty phase | |
| Tetradecafluorohexane | 10.0% |
| Cyclohexasiloxane | 5.0% |
| B-Aqueous phase | |
| AMPS polymer sold under the name "Hostacerin AMPS ® " by the company Clariant | 2.0% |
| Preserving agents | 0.2% |
| Glycerol | 5.0% |
| Water | 77.8% |

This gel-cream without surfactant (i.e., no emulsifier or detergent) was particularly suitable for gently removing make-up from sensitive and delicate skin.

What is claimed is:
1. A process for removing make-up from the skin or for cleansing the skin, comprising (1) applying an effective amount of a composition to skin, and (2) removing the composition from the skin, wherein the composition is anhydrous or aqueous, and wherein the composition contains at least one volatile fluoro compound in an amount of at least 0.5% by weight, relative to the total weight of said composition.

2. A process according to claim 1, wherein the composition contains the at least one volatile fluoro compound in an amount of at least 5% by weight, relative to the total weight of said composition.

3. A process according to claim 1, wherein the composition contains the at least one volatile fluoro compound in an amount ranging from 5 to 80% by weight, relative to the total weight of said composition.

4. A process according to claim 1, wherein the composition contains the at least one volatile fluoro compound in an amount ranging from 8 to 70% by weight, relative to the total weight of said composition.

5. A process according to claim 1, wherein the at least one volatile fluoro compound is chosen from perfluorocycloalkyls of formula (I):

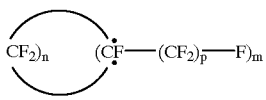
(I)

in which:

n is 3, 4 or 5, m is 1 or 2, and p is 1, 2 or 3, with the proviso that when m=2, the groups (CF—(CF$_2$)$_p$—F) are not necessarily alpha to each other.

6. A process according to claim 1, wherein the at least one volatile fluoro compound is chosen from perfluoroalkanes of formula (II):

(II)

in which:

m is 2 to 8, and

X is chosen from Br or F.

7. A process according to claim 1, wherein the at least one volatile fluoro compound is chosen from fluoroalkyls and heterofluoroalkyls of formula (III):

(III)

in which:

t is 0 or 1, n is 0, 1, 2 or 3,

X is chosen from linear and branched perfluoroalkyl radicals containing from 2 to 5 carbon atoms, and Z is chosen from O, S, or NR, wherein R is chosen from hydrogen and the radicals —(CH$_2$)$_n$—CF$_3$ and —(CF$_2$)$_m$—CF$_3$, wherein m is 2, 3, 4, or 5.

8. A process according to claim 1, wherein the at least one volatile fluoro compound is chosen from perfluoromorpholine derivatives of formula (IV):

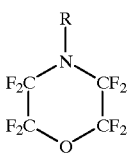
(IV)

in which:

R is a C$_1$–C$_4$ perfluoroalkyl radical.

9. A process according to claim 5, wherein the at least one volatile fluoro compound of formula (I) is chosen from perfluoromethylcyclopentane, perfluoro 1,3-dimethylcyclohexane, and perfluoro 1,2-dimethylcyclobutane.

10. A process according to claim 6, wherein the at least one volatile fluoro compound of formula (II) is chosen from dodecafluoropentane, tetradecafluorohexane, and bromoperfluorooctyl.

11. A process according to claim 7, wherein the at least one volatile fluoro compound of formula (III) is chosen from nonafluoromethoxybutane, and nonafluoroethoxyisobutane.

12. A process according to claim 8, wherein the at least one volatile fluoro derivative of formula (IV) is 4-trifluoromethylperfluoromorpholine.

13. A process according to claim 1, wherein the composition is in the form of an anhydrous oil containing the at least one volatile fluoro compound in soluble form or in a form which is finely dispersed in at least one cosmetic oil.

14. A process according to claim 13, wherein the at least one cosmetic oil is chosen from non-fluoro oils which are miscible with the at least one volatile fluoro compound.

15. A process according to claim 14, wherein the non-fluoro oils which are miscible with the at least one volatile fluoro compound are chosen from polysiloxanes.

16. A process according to claim 15, wherein the polysiloxanes are chosen from volatile polydimethylsiloxanes and volatile hydrocarbon based oils.

17. A process according to claim 16, wherein the volatile polydimethylsiloxanes are chosen from cyclopentasiloxane or cyclohexasiloxane.

18. A process according to claim 16, wherein the volatile hydrocarbon based oils are chosen from C$_{11}$–C$_{13}$ isoparaffins.

19. A process according to claim 13, wherein the at least one cosmetic oil is chosen from non-fluoro oils which are not miscible with the at least one volatile fluoro compound.

20. A process according to claim 19, wherein the non-fluoro oils which are not miscible with the at least one volatile fluoro compound are chosen from fatty acid esters containing at least 6 carbon atoms.

21. A process according to claim 20, wherein the non-fluoro oils which are not miscible with the at least one volatile fluoro compound are chosen from fatty acid esters containing at least 6 carbon atoms which are obtained from linear and branched C$_1$–C$_{17}$ alcohols and from linear and branched C$_6$–C$_{22}$ fatty acids.

22. A process according to claim 20, wherein the fatty esters are chosen from 2-ethylhexyl palmitate, 2-ethylhexyl myristate, isopropyl palmitate, isopropyl myristate, diisopropyl adipate, dioctyl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate, and isopropyl isostearate.

23. A process according to claim 1, wherein the at least one volatile fluoro compound is present in an amount ranging from 20 to 80% by weight, relative to the total weight of said composition.

24. A process according to claim 23, wherein the at least one volatile fluoro compound is present in an amount ranging from 30 and 65% by weight, relative to the total weight of said composition.

25. A process according to claim 1, further comprising a fatty phase and an aqueous phase, wherein the composition is in the form of a water-in-oil or oil-in-water emulsion.

26. A process according to claim 25, wherein the at least one volatile fluoro compound is present in soluble form or in a form dispersed in the fatty phase of the emulsion.

27. A process according to claim 26, wherein the fatty phase contains at least 5% by weight, based on the weight of the fatty phase, of said at least one volatile fluoro compound, and wherein said fatty phase represents from 2 to 70% by weight, relative to the total weight of said composition, and wherein said aqueous phase represents from 30 to 98% by weight, relative to the total weight of said composition.

28. A process according to claim 27, wherein the fatty phase of the composition represents from 5 to 30% by weight, relative to the total weight of said composition.

29. A process according to claim 1, wherein the aqueous phase of the composition represents from 30 to 98% by weight, relative to the total weight of said composition.

30. A process according to claim 29, wherein the aqueous phase of the composition represents from 70 to 95% by weight, relative to the total weight of said composition.

31. A process for removing make-up from the skin or for cleansing the skin, comprising (1) applying an effective amount of a composition to skin, and (2) removing the composition from the skin using a pad of cotton wool, optionally soaked in water, wherein the composition is anhydrous or aqueous, and wherein the composition contains at least one volatile fluoro compound in an amount of at least 0.5% by weight, relative to the total weight of said composition.

* * * * *

UNITED STATES PATENT AND TRADEMARK OFFICE
CERTIFICATE OF CORRECTION

PATENT NO.    : 6,383,998 B1
DATED         : May 7, 2002
INVENTOR(S)   : Raluca Lorant It is certified that error appears in the above-identified patent and that said Letters Patent is hereby corrected as shown below:

<u>Column 2,</u>
Lines 45-50, formula (IV), "$_2$C" (both occurrences) should read -- $F_2C$ --.

<u>Column 7,</u>
Line 57, "0 or 1" should read -- 0 or 1 --.

Signed and Sealed this

Thirtieth Day of July, 2002

*Attest:*

JAMES E. ROGAN
*Attesting Officer*    *Director of the United States Patent and Trademark Office*